United States Patent [19]

Geary

[11] 4,273,419
[45] Jun. 16, 1981

[54] LIGHT-SCATTERING DISC COLLECTOR

[75] Inventor: Joseph M. Geary, Edgewood, N. Mex.

[73] Assignee: The United States of America as represented by the Secretary of the Air Force, Washington, D.C.

[21] Appl. No.: 132,451

[22] Filed: Mar. 21, 1980

[51] Int. Cl.$^3$ ............... G02B 5/02; G01N 21/00
[52] U.S. Cl. ..................... 350/320; 356/432; 350/431
[58] Field of Search ............ 350/17, 188, 87, 314, 350/320; 356/432, 443, 444; 362/355, 259

[56] References Cited

U.S. PATENT DOCUMENTS

| | | | |
|---|---|---|---|
| 3,802,784 | 4/1974 | Reynolds et al. | 356/432 |
| 4,025,200 | 5/1977 | Zeineh | 356/432 |

Primary Examiner—Jon W. Henry
Attorney, Agent, or Firm—Donald J. Singer; Arsen Tashjian

[57] ABSTRACT

A light-scattering disc collector member useable in converting a classical (coherence-dependent) microdensitometer to a linear (mode) microdensitometer that is coherence-independent. The member is made of material that is transmissive, non-absorbing, and high scattering as to light, and it preferably comprises a right circular cylinder which is made opaque (such as with black paint), except for a light-transmissive entrance aperture which is located on one base of the cylinder and which is shaped as an inwardly formed hemispherical dome, and a light-transmissive exit aperture which is located on the other base of the cylinder in geometric alignment with the entrance aperture. When used to convert a classical microdensitometer to a linear microdensitometer, the light-scattering disc collector member replaces the objective of the microscope in the sensor optics assembly of the classical microdensitometer.

8 Claims, 8 Drawing Figures

LIGHT-SCATTERING DISC COLLECTOR

STATEMENT OF GOVERNMENT INTEREST

The invention described herein may be manufactured and used by or for the Government for governmental purposes without the payment of any royalty thereon.

BACKGROUND OF THE INVENTION

This invention relates generally to microdensitometers and, more particularly, to a unique light-scattering disc collector member (and assembly) which has many applications, including: use as a constituent of a sensor optics assembly of a microdensitometer; and, more importantly, use as a replacement of pertinent structural members of a sensor optics assembly of a classical microdensitometer, whereby the classical microdensitometer is converted to a linear microdensitometer.

As will be shown later, a classical microdensitometer is, essentially, two opposing microscopes: one to irradiate the target or object sample (i.e., "source optics"); and, the other to sample target (or object sample) radiance (i.e., "sensor optics") as a function of position.

It is well known in the microdensitometer art that the use of a classical microdensitometer inherently results in significantly misleading information at the output end of the classical microdensitometer system, because of coherent diffraction at the site of the target (or object sample), coupled with the imaging function of the sensor optics. Unfortunately, there is little that can be done about the increasingly felt effects of coherence as one moves toward greater system resolution, as long as a classical microdensitometer is used.

Therefore, what is needed in the art, and is not presently available, is (for reasons that will be explained later herein) a means for (and/or a method of) converting a classical microdensitometer to a linear (mode) microdensitometer, easily and economically.

My invention fulfills this existing need and, thereby, constitutes a significant advance in the state-of-the-art.

SUMMARY OF THE INVENTION

My invention pertains to a unique light-scattering disc collector (and assembly) and a novel method of making same, which said disc collector has many applications, including use as an easy and economical replacement of pertinent structural members of a sensor optics assembly of a classical microdensitometer, such that the microdensitometer is thereby converted to a linear (mode) microdensitometer.

Accordingly, the principal object of my invention is to teach the structure of a preferred embodiment of the above-described unique light-scattering disc collector (and assembly thereof).

Another object of my invention is to teach a novel, and preferred, method of making the preferred embodiment of my unique light-scattering disc collector (and assembly).

Still another object of my invention is to teach the use of my disc collector assembly as a constituent subassembly of a sensor optics assembly of a microdensitometer.

Yet another object of my invention is to teach a novel method of converting a classical microdensitometer to a linear (mode) densitometer with, and by the use, of my unique light-scattering disc collector (and assembly thereof).

These objects of my invention, as well as other objects (e.g., simplification of calibration problems, and elimination of the effects of flare light), will become readily apparent after a consideration of the description of my invention, together with reference to the Figures of the drawings, in which the same reference character refers to the same component.

DESCRIPTION OF THE DRAWINGS

FIGS. 2A and 2B are perspective views, in simplified pictorial form of the preferred embodiment of my light-scattering disc collector, whereas

It is to be noted that FIGS. 2-5, inclusive, also show the results of practicing the steps of my inventive methods which will be discussed later herein.

DESCRIPTION OF THE PREFERRED EMBODIMENT

Figure 2A:
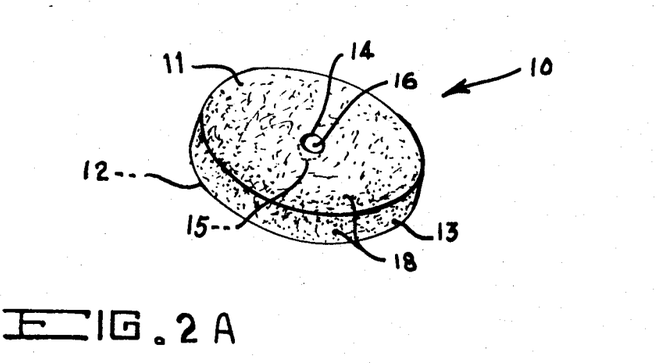
Figure 2B:
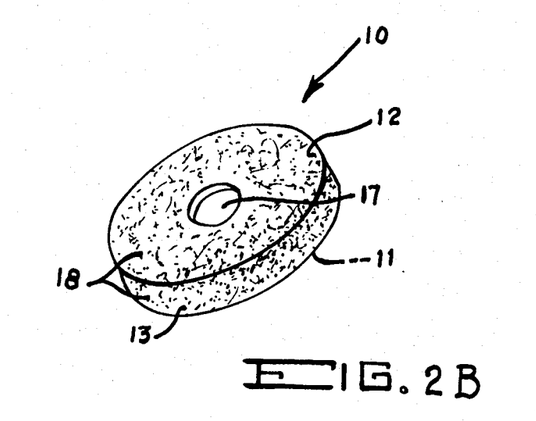
Figure 2C:
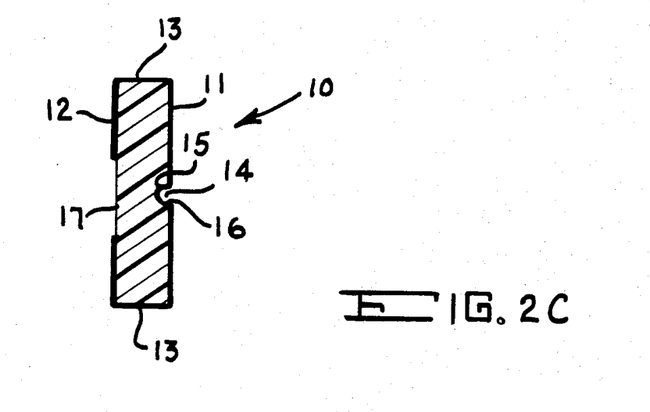
FIG. 2C is a side elevation view, in cross section, of the same embodiment.

With reference to FIGS. 2A, 2B and 2C, therein is shown in different views the preferred embodiment 10 of my unique light-scattering disc collector member.

The member 10 is made of material which transmits light and also is non-absorbing and highly scattering as to light. More specifically, the member 10 has a first flat face 11 and a second flat face 12 which are opaque to light, and which are in parallel-space relationship with each other, with the first and the second flat faces 11 and 12 joined by a common surface 13 which is opaque to light. The first flat face 11 has a light-transmissive entrance aperture 14 therein which is in the form of a cavity that is in the shape of an inwardly disposed hemispherical dome 15 that is anti-reflective coated 16. The second flat face 12 has a light-transmissive exit aperture 17 that is in optical alignment with the light-transmissive entrance aperture 14 in the first flat face 11.

As a matter of preference, and not of limitation, my light-scattering disc collector member 10 is made of a plastic material; and the member 10 is in the shape of a right circular cylinder having a cylindrical surface 13, with the first flat face 11 comprising a base of the cylinder, and with the second flat face 12 comprising the other base of the cylinder, and also with the common surface 13 which is joining the first and the second flat faces 11 and 12 comprising the cylindrical surface 13 of the cylinder; and, the exit aperture 17 is also in geometric alignment (as distinguished from the more generic "optical alignment") with the entrance aperture 14 and is in the shape of a circle 17 which is concentric with the inwardly disposed hemispherical dome-shaped entrance aperture 14.

Figure 3:
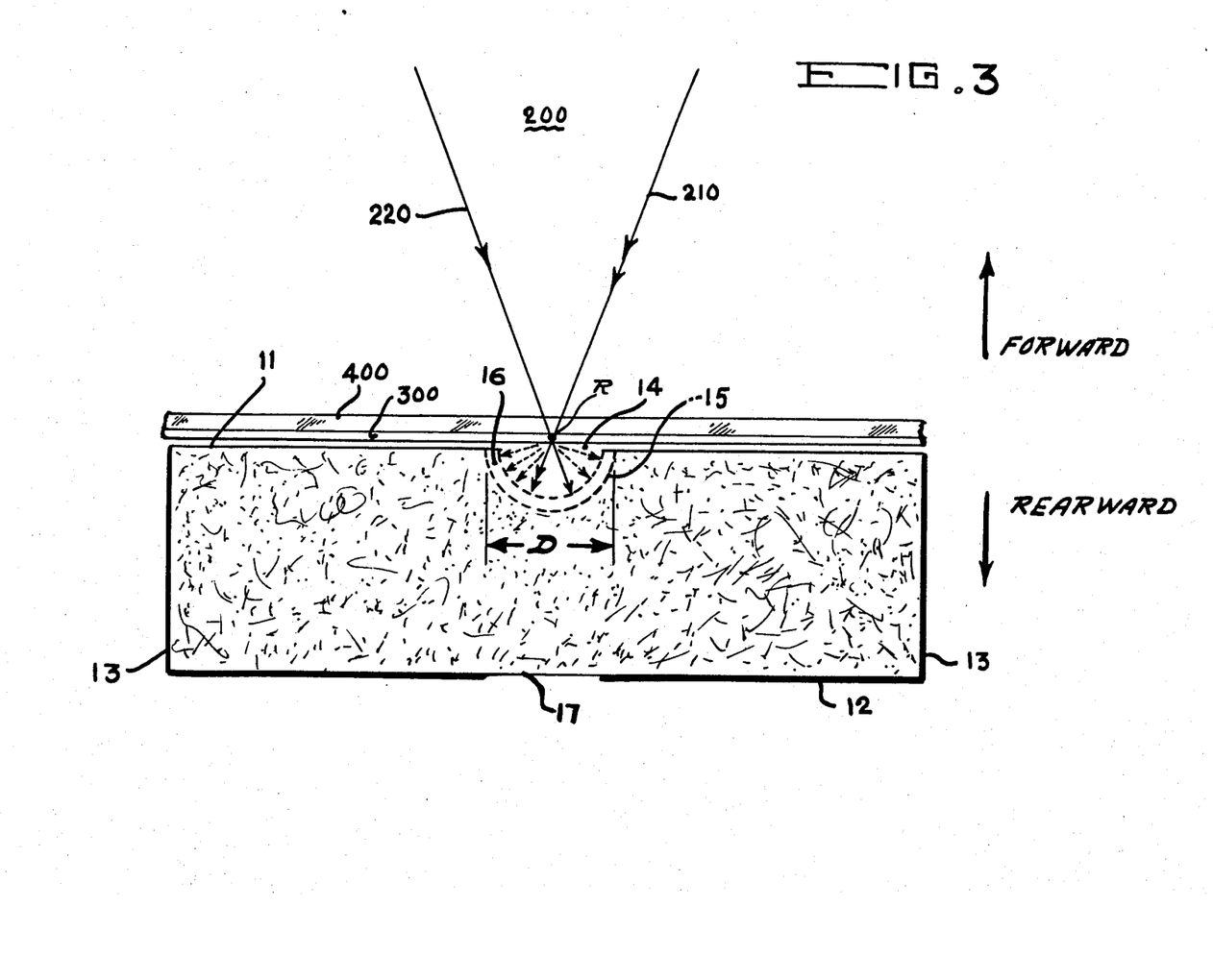
FIG. 3 is a top plan view, in simplified pictorial and schematic form, of the preferred embodiment of my light-scattering disc collector in its working environment.

With reference to FIG. 3, therein is shown my light-scattering disc collector member 10 in its working environment which includes, but is not limited to, a beam of light 200 that is defined by representative edge rays 210 and 220 and that is focused on, and impinges upon, the target (or object sample) 300 which is disposed forward of the first flat face 11 and is supported by a suitable transparent means 400, such as glass.

It is here to be noted that, as shown in FIG. 3, the hemispherical dome 15 has a diameter "D" which is much larger (i.e., longer) than the irradiated region "R" on the object plane 300 which is located at the radius of curvature of the hemispherical dome 15. Light-scattering within the dome 15 is represented schematically by the dotted arrows.

Figure 4:
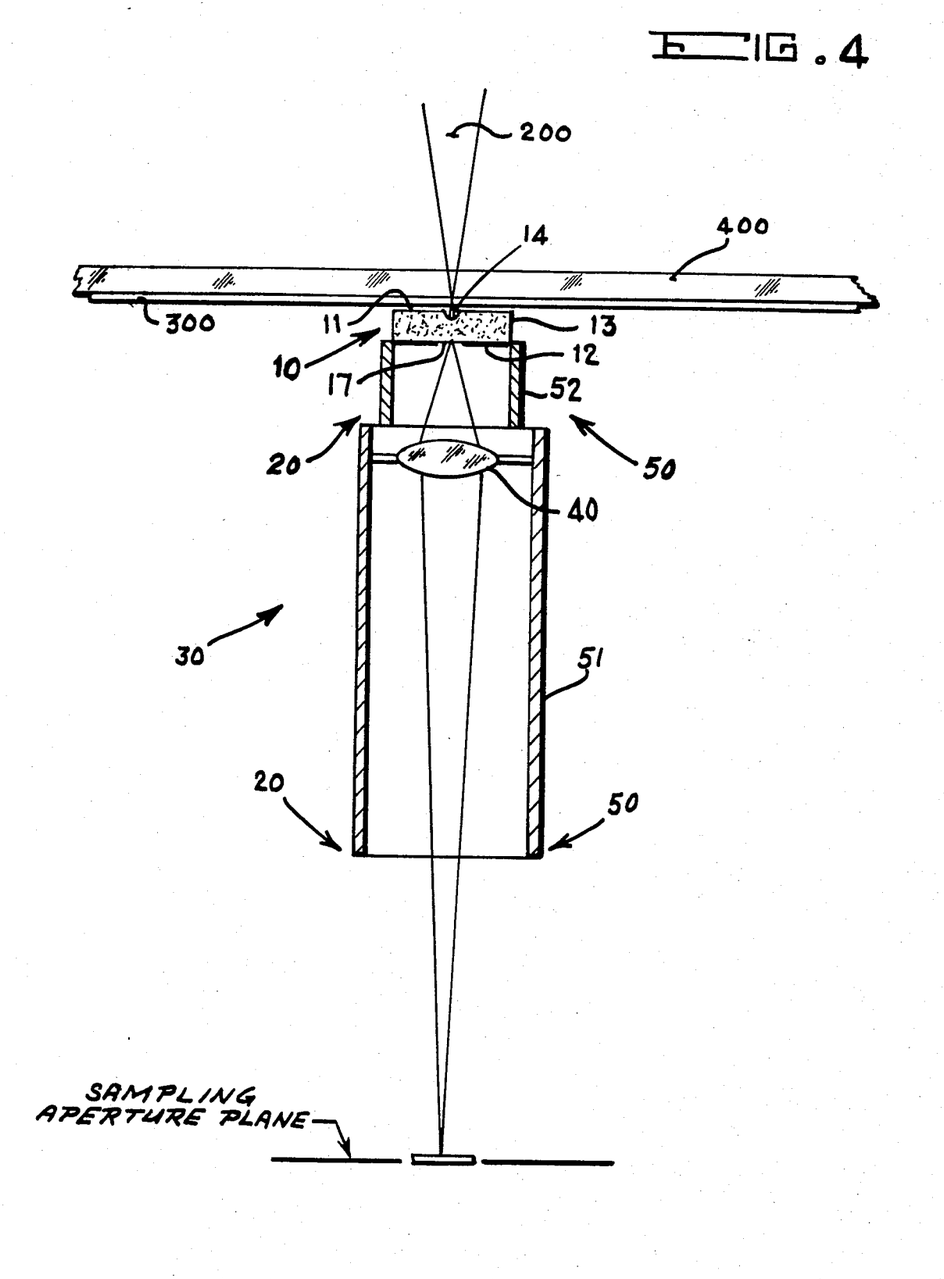
FIG. 4 is a top plan view, in simplified pictorial and schematic form, of the preferred embodiment of my light-scattering disc collector as it comprises a component of a novel assembly that is shown in use in its working environment as a constituent subassembly of a sensor optics assembly of a microdensitometer.

With reference to FIG. 4, therein is shown my light-scattering disc collector member 10, as it is structurally incorporated as one component in my novel assembly 20 which hereinafter I will refer to as the "light-scattering disc collector assembly". However, it will be noted that, as shown in FIG. 4, my light-scattering disc collector assembly 20 in turn comprises actually a constituent subassembly of a sensor optics assembly 30, FIG. 4 (which is similar to the sensor optics assembly 110, FIG. 1), of a classical microdensitometer.

Still with reference to FIG. 4, my light-scattering disc collector assembly 20 (i.e., the constituent subassembly 20 of the sensor optics assembly 30) comprises: my light-scattering disc collector member 10, as hereinbefore structurally described; and, a relay lens 40 disposed rearward of, and in optical alignment with, the light-scattering disc collector 10; and also, a means (generally designated 50) for holding the light-scattering disc collector 10 and the relay lens 40 in optical alignment, where this means 50 includes (as a matter of preference) a microscope barrel 51 and an associated tube extender 52, as shown in FIG. 4.

Also, as a matter of preference, and not of limitation, the light-transmissive exit aperture 17 in the second flat face 12 of the collector member 10 also is in geometric alignment with the light-transmissive entrance aperture 14 in the first flat face 11 of the collector member 10; and, the relay lens 40 also is in geometric alignment with the collector member 10; and also, the holding means 50 also holds the collector member 10 and the relay lens 40 also in geometric alignment.

DESCRIPTION OF THE INVENTIVE METHODS

Figure 1:
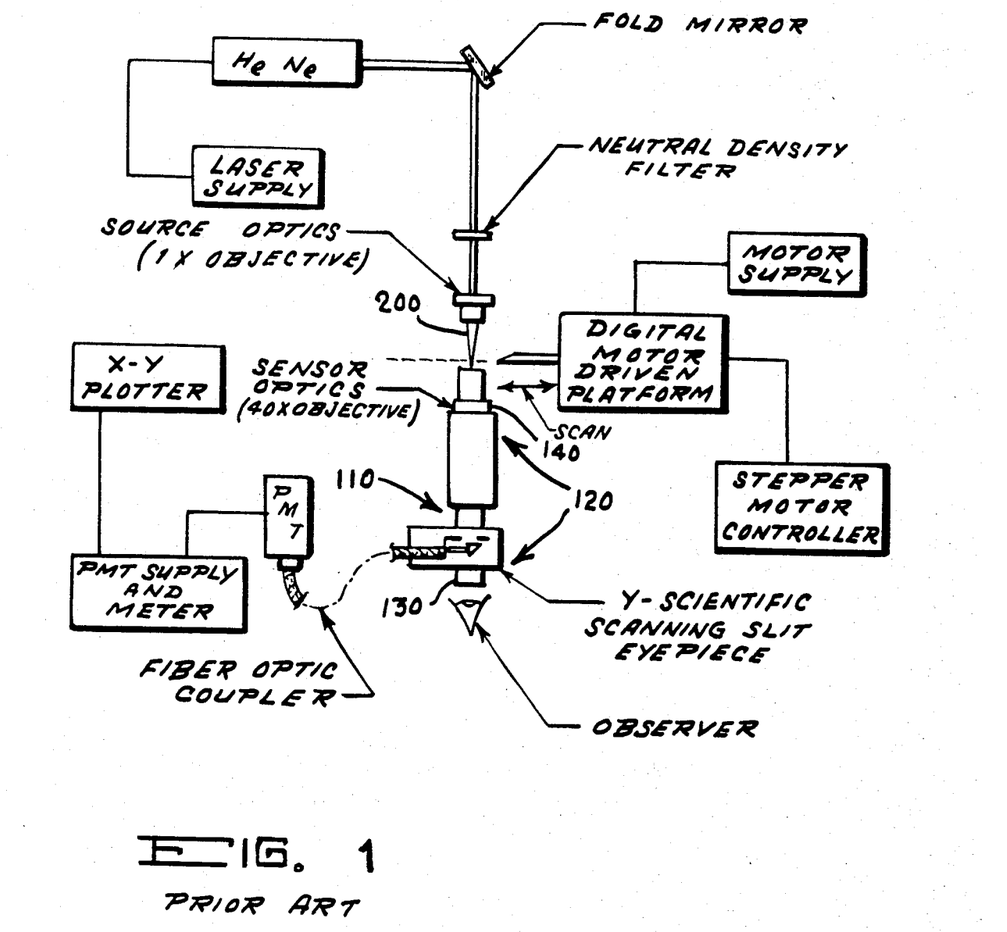
FIG. 1 is a top plan view, in simplified pictorial and schematic form, of a typical prior art classical microdensitometer.
Figure 5:
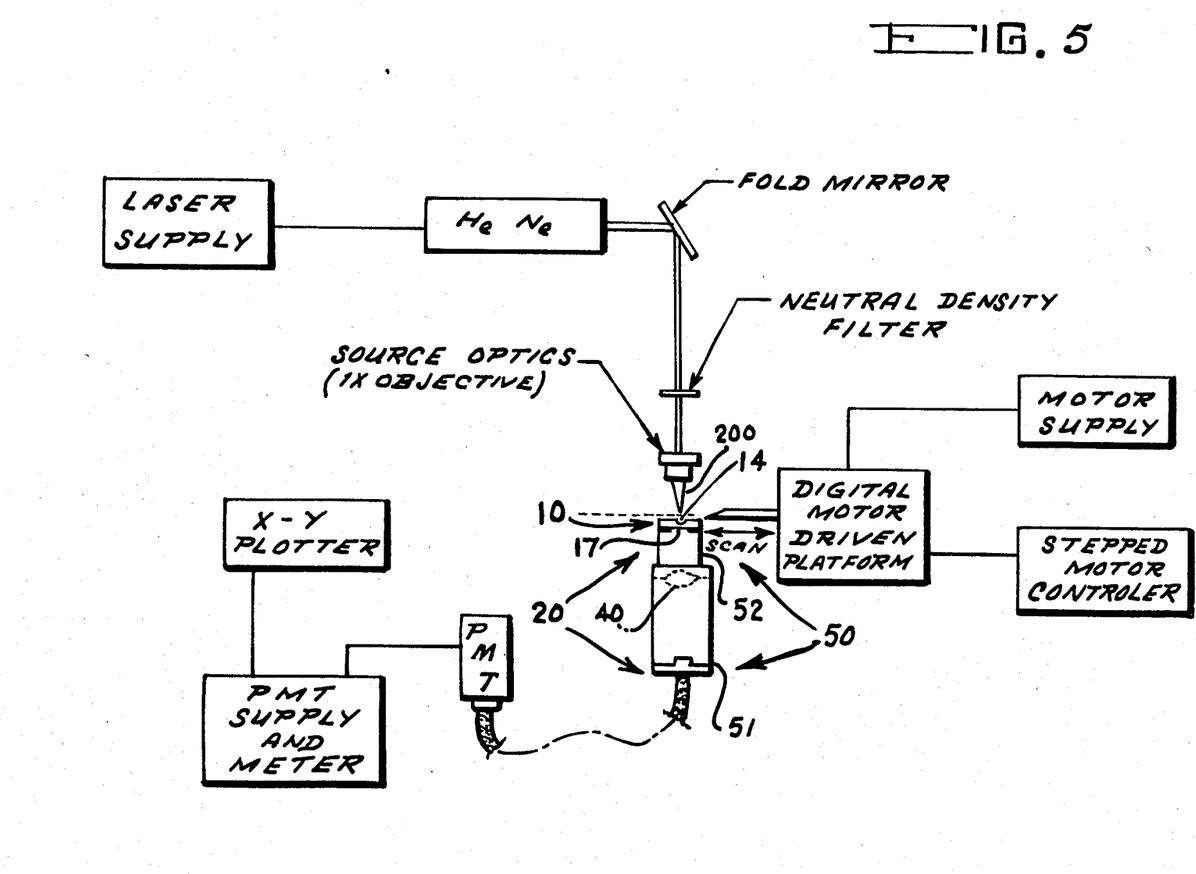
FIG. 5 is a top plan view, in simplified pictorial and schematic form, of my light-scattering disc collector assembly substituted for pertinent structural members of the usual sensor optics assembly in a classical microdensitometer, such as is shown in FIG. 1, whereby the classical microdensitometer is converted to a linear (mode) microdensitometer.

My inventive methods are two. One of the methods comprises the steps of making my light-scattering disc collector 10; and, the other method comprises the steps of converting a classical microdensitometer (such as 100, as is shown in FIG. 1) to a linear (mode) microdensitometer (such as 500, as is shown in FIG. 5). In this regard, and as a preliminary matter, reference is made to FIGS. 2-5, inclusive, which show the results of practicing the steps of my two above-mentioned methods.

My inventive method of making my light-scattering disc collector 10 comprises, essentially, six steps. They are:

Firstly, forming a right circular cylinder member from material which is transmissive, non-absorbing, and highly scattering as to light, wherein the cylinder member has a first flat face 11 as a base, a second flat face 12 as another base, and a cylindrical surface 13 which joins and is common to the flat faces 11 and 12; and Next, coating the cylinder member with a material 18, FIGS. 2A and 2B, which is opaque to light; and Then, removing a preselected circular portion of the opaque coating 18 from the first flat face 11 of the cylinder member; and Next, forming a light-transmissive entrance aperture 14, in the form of a cavity which is in the shape of an inwardly disposed hemispherical dome 15, in the first flat face 11 at where the opaque coating 18 has been removed; and Then, coating the cavity with a material 16 which is antireflective as to light; and Lastly, removing a preselected circular portion of the opaque coating 18 from the second flat face 12 of the cylinder member, where the preselected circular portion is in geometric alignment with and is concentric to the entrance aperture 14, thereby forming a light-transmissive exit aperture 17.

As the result of practicing these steps, my light-scattering disc collector member 10 is formed.

My method of converting a classical microdensitometer 100, FIG. 1, to a linear (mode) microdensitometer 500, FIG. 5, where the classical microdensitometer 100 includes a sensor optics assembly 110, FIG. 1, which further includes a sensor microscope 120, FIG. 1, having an eyepiece 130 and objective 140, comprises, essentially, three steps. They are:

Firstly, removing the eyepiece 130 of the sensor microscope 120; and

Then, removing the objective 140 of the sensor microscope 120; and

Lastly, substituting my light-scattering disc collector assembly 20, FIG. 4, as hereinbefore described structurally (i.e., my light-scattering disc collector member 10, and the relay lens 40, and also the means 50 for holding the collector member 10 and the relay lens 40 in optical, or geometric, alignment).

As a result of the practicing of these steps, the classical microdensitometer 100, FIG. 1, is converted to the linear (mode) microdensitometer 500, FIG. 5.

MANNER OF OPERATION OF THE PREFERRED EMBODIMENT

The manner of operation, and of use, of the preferred embodiment of my light-scattering disc collector member 10, FIGS. 2-5, and of my light-scattering disc collector assembly 20, FIGS. 4 and 5, can be easily ascertained by any person of ordinary skill in the art from the foregoing description of my collector member 10 and of my collector assembly 20, coupled with reference to the contents of the Figures of the drawings and the description of the two methods. With regard to the latter, and particularly my method of converting the classical microdensitometer 100, FIG. 1, to the linear (mode) microdensitometer 500, FIG. 5, my basic approach was that if the sensor optics 110, FIG. 1, were no longer used in an imaging mode, and if the replacement sensor optics 20, FIGS. 5 and 4, could (as they do) catch all of the light 200 leaving the target (or object sample) 300, FIGS. 1, 3, 4 and 5, so that the output is directly proportional to it, then the coherence of light would no longer matter, the structure (i.e., pattern) due to diffraction would not show up in the output, and the sampling aperture would be defined by the source optics (rather than the combination of the coherent diffraction at the site of the target, coupled with the imaging function of the sensor optics).

CONCLUSION

It is abundantly clear from all of the foregoing, and from the Figures of the drawings, that the stated objects (as well as related objects) of my invention have been achieved.

Figure 6:
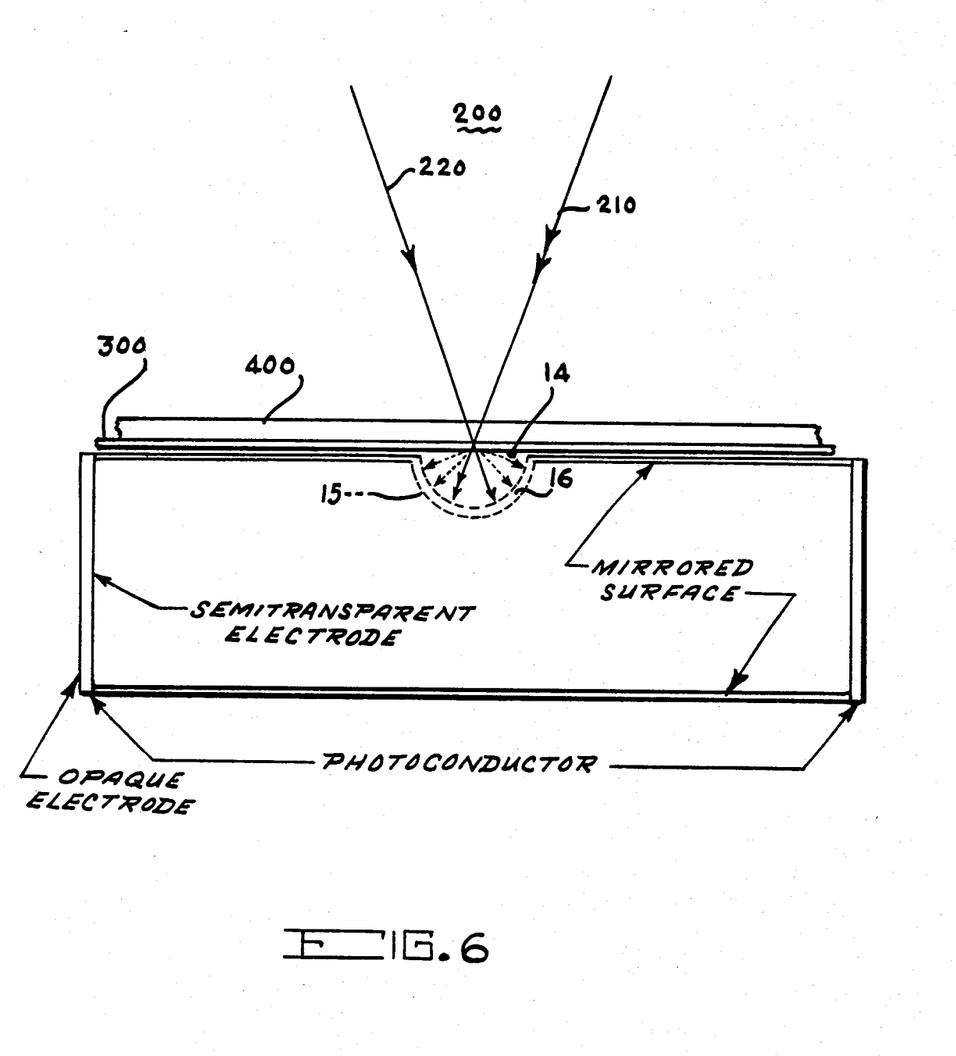
FIG. 6 is a variation of the preferred embodiment of my light-scattering disc collector member, if certain restraints in function of the member could be removed.

It is to be noted that, although there have been described and shown the fundamental and unique features of my invention as applied to preferred embodiments, various other embodiments, variations, adaptations, substitutions, additions, omissions, and the like may occur to, and can be made by, those of ordinary skill in the art, without departing from the spirit of my invention. For example, and with reference to FIG. 6: If my light-scattering disc collector member 10 did not have to be structured such that it could be used in existing classical microdensitometers, then it could also be structured (as a variation) as shown in FIG. 6, to wit: the exit aperture could be eliminated, and the detector surface could be incorporated within the walls of the cylinder.

Additionally, because of my teaching, it may occur to others of ordinary skill in the art that, in appropriate circumstances, the number of the basic and fundamental steps of my two inventive methods can be increased, decreased, eliminated, or otherwise varied. For example, and with regard to the method of making my light-scattering disc collector member 10, the surfaces of that member 10 can be painted after (rather than before) the entrance aperture 14 is formed and the exit aperture 17 is defined.

What is claimed is:

1. A light-scattering disc collector comprising a member made of material which transmits light and also is non-absorbing and highly scattering as to said light, wherein:
    (a) said member has a first flat face and a second flat face which are opaque to light, and which are in parallel-spaced relationship with each other;
    (b) said first and second flat faces are joined by a common surface which is opaque to light;
    (c) said first flat face has a light-transmissive entrance aperture therein in the form of a cavity which is in the shape of an inwardly disposed hemispherical dome that is light-antireflective coated;
    (d) and, said second flat face has a light-transmissive exit aperture in optical alignment with said light-transmissive entrance aperture in said first flat face.

2. A light-scattering disc collector, as set forth in claim 1, wherein:
    (a) said member is in the shape of a right circular cylinder having a cylindrical surface, with said first flat face comprising, a base of said cylinder, and with said second flat face comprising another base of said cylinder, and also with said common surface which is joining said first and said second flat faces comprising said cylindrical surface of said cylinder;
    (b) and, said exit aperture is also in geometric alignment with said entrance aperture, and is in the shape of a circle which is concentric with said inwardly disposed hemispherical dome-shaped entrance aperture.

3. A light-scattering disc collector, as set forth in claim 2, wherein said member is made of a plastic material.

4. A method of making a light-scattering disc collector, comprising the steps of:
    (a) forming a right circular cylinder member from material which is transmissive, non-absorbing, and highly scattering as to light, wherein said cylinder member has a first flat face as a base, a second flat face as another base, and a cylindrical surface which joins and is common to said flat faces;
    (b) coating said cylinder member with a material which is opaque to light;
    (c) removing a preselected circular portion of said opaque coating from said first flat face of said cylinder member;
    (d) forming a light-transmissive entrance aperture, in the form of a cavity which is in the shape of an inwardly disposed hemispherical dome, in said first flat face at where said opaque coating has been removed;
    (e) coating said cavity with a material which is antireflective as to light;
    (f) and, removing a preselected circular portion of said opaque coating from said second flat face of said cylinder member, wherein said preselected circular portion is in geometric alignment with and is concentric to said entrance aperture, thereby forming a light-transmissive exit aperture.

5. A constituent light-scattering disc collector subassembly of a sensor optics assembly of a microdensitometer, comprising:
    (a) a light-scattering disc collector having a first flat face and a second flat face which are opaque to light, and which are in parallel-spaced relationship with each other, wherein said first and second flat faces are joined by a common surface which is opaque to light, and wherein said first flat face has a light-transmissive entrance aperture therein in the form of a cavity which is in the shape of an inwardly disposed hemispherical dome that is light-antireflective coated, and also wherein said second flat face has a light-transmissive exit aperture in optical alignment with said light-transmissive entrance aperture in said first flat face;
    (b) a relay lens disposed rearward of, and in optical alignment with, said light-scattering disc collector;
    (c) and, means for holding said light-scattering disc collector and said relay lens in optical alignment.

6. A constituent light-scattering disc collector subassembly of a sensor optics assembly of a microdensitometer, as set forth in claim 5, wherein said light-transmissive exit aperture in said second flat face of said light-scattering disc collector also is in geometric alignment with said light-transmissive entrance aperture in said first flat face, and wherein said relay lens also is in geometric alignment with said light-scattering disc collector, and also wherein said holding means also holds said light-scattering disc collector and said relay lens in geometric alignment.

7. A method of converting a classical microdensitometer to a linear microdensitometer, wherein said classical microdensitometer includes a sensor optics assembly which further includes a sensor microscope having an eyepiece and an objective, comprising the steps of:
    (a) removing said eyepiece of said sensor microscope;
    (b) removing said objective of said sensor microscope;
    (c) and substituting a light-scattering disc collector assembly for said objective of said sensor microscope, wherein this assembly comprises:

(1) a light-scattering disc collector having a first flat face and a second flat face which are opaque to light, and which are in parallel-spaced relationship with each other, wherein said first and said second flat faces are joined by a common surface which is opaque to light, and wherein said first flat face has a light-transmissive entrance aperture therein in the form of a cavity which is in the shape of an inwardly disposed hemispherical dome that is light-antireflective coated, and also wherein said second flat face has a light-transmissive exit aperture in optical alignment with said light-transmissive entrance aperture in said first flat face;

(2) a relay lens disposed rearward of, and in optical alignment with, said scattering disc collector;

(3) and, means for holding said scattering disc collector and said relay lens in optical alignment.

8. A method of converting a classical microdensitometer to a linear microdensitometer, as set forth in claim 7, wherein in said light-scattering disc collector assembly which is substituted for said objective of said sensor microscope, said light-transmissive exit aperture in said second flat face of said light-scattering disc collector also is in geometric alignment with said light-transmissive entrance aperture in said first flat face, and said relay lens also is in geometric alignment with said light-scattering disc collector, and said holding means holds said light-scattering disc collector and said relay lens in geometric alignment.

* * * * *